(12) United States Patent
Lipkowski et al.

(10) Patent No.: US 9,365,633 B2
(45) Date of Patent: Jun. 14, 2016

(54) PEPTIDE PREPARATIONS AND PEPTIDES WITH ANTITUMOUR ACTIVITY

(75) Inventors: Andrzej Lipkowski, Warsaw (PL); Sergiusz Markowicz, Warsaw (PL)

(73) Assignee: Instytut Medycyny Doswiadczalnej I Klinicznej Pan, Warsaw (PL)

( * ) Notice: Subject to any disclaimer, the term of this patent is extended or adjusted under 35 U.S.C. 154(b) by 0 days.

(21) Appl. No.: 13/992,023

(22) PCT Filed: Dec. 6, 2011

(86) PCT No.: PCT/PL2011/050049
§ 371 (c)(1),
(2), (4) Date: Jun. 25, 2013

(87) PCT Pub. No.: WO2012/078060
PCT Pub. Date: Jun. 14, 2012

(65) Prior Publication Data
US 2014/0315824 A1    Oct. 23, 2014

(30) Foreign Application Priority Data
Dec. 6, 2010 (PL) ......................................... 393153

(51) Int. Cl.
*C07K 14/78* (2006.01)
*C07K 7/06* (2006.01)
*C07K 7/08* (2006.01)
*C07K 14/435* (2006.01)
*A61K 38/00* (2006.01)

(52) U.S. Cl.
CPC . *C07K 14/78* (2013.01); *C07K 7/06* (2013.01); *C07K 7/08* (2013.01); *C07K 14/435* (2013.01); *A61K 38/00* (2013.01)

(58) Field of Classification Search
CPC ...... A61K 38/00; C07K 14/435; C07K 14/78; C07K 7/06; C07K 7/08
See application file for complete search history.

(56) References Cited

U.S. PATENT DOCUMENTS 5,527,773 A    6/1996   Steinert et al.
2004/0006205 A1 *  1/2004  Li et al. ........................ 530/350

FOREIGN PATENT DOCUMENTS

FR           2883168 A1 *  9/2006  ............... A61K 7/06

OTHER PUBLICATIONS

UniProt Protein Database, Protein Accession Q28580, Keratin-associated protein 7-1, accessed on Nov. 24, 2014.*
Patent Translate, EPO and Google, English Tranlsation of the Description of FR2883168, accessed on Nov. 24, 2014.*
Lipkowski et al., "Keratin-associated protein micromaterials for medical and cosmetic applications," Polimery (2009); 54(5):386-388.
Jones et al., "Bioprospecting keratinous materials," International Journal of Trichology (2010); 2(1):47-49.

* cited by examiner

*Primary Examiner* — James H Alstrum Acevedo
*Assistant Examiner* — Erinne Dabkowski
(74) *Attorney, Agent, or Firm* — Fox Rothschild LLP; Shahnam Sharareh

(57) ABSTRACT

The subject of the present invention are peptide preparations obtained via the enzymatic digestion of hair, wool, bristles, animal fur and individual peptides with sequences corresponding to individual components of a peptide preparation with antitumor activity, for use in the treatment of tumors or oncological prophylaxis as basal components or components of compositions of substances for treating tumors or components of substances used in oncological prophylaxis.

8 Claims, No Drawings

PEPTIDE PREPARATIONS AND PEPTIDES WITH ANTITUMOUR ACTIVITY

This application is a U.S. National Phase Application of International Application No. PCT/PL2011/050049 filed Dec. 6, 2011, which claims priority to Polish Application No. 393153 filed December 6, the disclosures of which are hereby incorporated by reference in their entirety.

The subject of the present invention are peptide preparations produced as a result of the enzymatic digestion of hair, wool, bristles, animal fur and individual peptides with sequences corresponding to individual components of peptide preparations with antitumour activity for use in the treatment of tumours or oncological prophylaxis as basal components or components of compositions of substances for treating tumours or components of substances used in oncological prophylaxis.

It is commonly accepted that hair, fur and bristles constitute natural, physical protection for an organism against mechanical trauma and thermal protection against excessive heat gain/loss. However, despite the great resistance against natural factors that degrade hair, fur or bristles, there exists the possibility of degrading their component proteins by the enzymes of bacteria and fungi that colonize the skin as well as by endogenous enzymes secreted in sweat. It is also observed that animals lick and swallow their fur, which may be partially degraded in the digestive tract, thereby secreting appropriate peptide fragments. Attempts have been made to seek the biological role of peptides constituting hair, fur or bristles. Patent WO 03/064449 describes and claims the use of active peptides from hair or wool in wound healing. Our studies on the conversion of hair or fur or bristles have made it possible to formulate an original method of converting using chemical activation and then pepsin digestion. This method was described and claimed in 1995 by B. Baranowska, A. W. Lipkowski, E. Marczak, I. Makulec, H. Rybak, J. Pastuszak, in "A method of activating keratinous substances by enzymatic hydrolysis", Polish Patent Nr 179342.

While studying the biological activity of a preparation produced through the enzymatic digestion of hair or wool or animal fur substrates initially activated by alkali activity, it unexpectedly turned out that these preparations exhibit significant antitumour activity against tumours of various aetiology. Further analysis of the peptides constituting the preparations showed that individual component peptides also demonstrate antitumour activity. For this reason, peptide preparations obtained through the appropriate digestion of hair or wool or animal fur may be used as active ingredients in the treatment or prophylaxis of tumours or that constitute components of substances for treatment or prophylaxis.

Examples of activities are given to better illustrate the present invention, the antitumour activities of the resulting preparations or individual component peptides. The scope of the present invention, however, should not be limited solely to the wording of the following examples.

EXAMPLE 1

Hair from a 60-year old man was activated and hydrolysed with pepsin according to the method described in A. W. Lipkowski, B. Gajkowska, A. Grabowska, K. Kurzepa, "Keratin-associated protein micromaterials for medical and cosmetic applications.", Polimery, Vol. 54, p. 386-388, 2009.

Hair (20 g) has been stirred in 0.1 N sodium hydroxide in room temperature for 2 hours. Then hair was filtered off and washed twice with water. Residue has been suspended in water, temperature has been adjusted to 40° C. pH has been adjusted with 10% hydrochloric acid to 1.6. Pepsin (5 mg) has been added and reaction mixture has been stirred at 40° C. The pH has been controlled and adjusted to pH 1.6-1.9 with hydrochloric acid. After 5 hours solid residue has been washed out, and filtrate has been heated to 80° C. and after 3 minutes, frozen down to −20° C. temperature, and lyophilised. The residual powder has been used for biological assays.

The portion dissolved as a result of pepsin digestion was yielding the preparation for further experiments. An analysis of the peptides in the preparation demonstrated the presence of peptides with the sequences given in the table and larger peptide with sequences given in the table.

TABLE

| Item. | Identified short peptide sequences in the preparation obtained from human hair (amino-acid residues given in the standard single-lettercode) |
|---|---|
| SEQ ID NO: 1 | AEIRSDL |
| SEQ ID NO: 2 | VVQIDNAKL |
| SEQ ID NO: 3 | LVVQIDNAKL |
| SEQ ID NO: 4 | NKQVVSSSEQL |
| SEQ ID NO: 5 | LNKQVVSSSEQL |
| SEQ ID NO: 6 | RQLVESDINGL |
| SEQ ID NO: 7 | TESEARYSSQL |
| SEQ ID NO: 8 | VVQIDNAKLAADDF |
| SEQ ID NO: 9 | NRVLNETRSQYEAL |
| SEQ ID NO: 10 | NKQVVSSSEQLQSYQAEIIELR |
| SEQ ID NO: 11 | NKQVVSSSEQLQSYQAEIIEL |
| SEQ ID NO: 12 | LNKQVVSSSEQLQSYQAEIIEL |
| SEQ ID NO: 13 | VVNIDNAKL |
| SEQ ID NO: 14 | NKQVVSSSEQL |
| SEQ ID NO: 15 | LNKQVVSSSEQL |
| SEQ ID NO: 16 | NVEVDTAPTVDL |
| SEQ ID NO: 17 | VVNIDNAKLASDDF |
| SEQ ID NO: 18 | VVEIDNAKL |
| SEQ ID NO: 19 | IQEIDF |
| SEQ ID NO: 20 | IDKVRF |
| SEQ ID NO: 21 | LEQQNKL |
| SEQ ID NO: 22 | ASELNHVQEVL |
| SEQ ID NO: 23 | NQQVVSSSEQL |
| SEQ ID NO: 24 | NQQVVSSSEQL |
| SEQ ID NO: 25 | RQLVESDINGL |
| SEQ ID NO: 26 | VVEIDNAKLAADDF |
| SEQ ID NO: 27 | IVQIDNAKLAADDF |
| SEQ ID NO: 28 | TVIFDTGSSNL |

TABLE-continued

Identified short peptide sequences in the preparation obtained from human hair (amino-acid residues given in the standard single-lettercode)

| Item. | Sequence |
|---|---|
| SEQ ID NO: 29 | GILGPVIKAEVGDTL |
| SEQ ID NO: 30 | IQEIDF |
| SEQ ID NO: 31 | IDKVRF |
| SEQ ID NO: 32 | VVQIDNAKL |
| SEQ ID NO: 33 | AEIRSDL |
| SEQ ID NO: 34 | AEIRSDLE |
| SEQ ID NO: 35 | AEIRSDL |
| SEQ ID NO: 36 | VVQIDNAKLA |
| SEQ ID NO: 37 | VVQIDNAKL |
| SEQ ID NO: 38 | NETRSQYEAL |
| SEQ ID NO: 39 | NKQVVSSSEQLQ |
| SEQ ID NO: 40 | NKQVVSSSEQL |
| SEQ ID NO: 41 | LNKQVVSSSEQL |
| SEQ ID NO: 42 | RQLVESDINGL |
| SEQ ID NO: 43 | VVQIDNAKLAADDF |
| SEQ ID NO: 44 | SQVQSLITNVESQL |
| SEQ ID NO: 45 | SQVQSLITNVESQLA |
| SEQ ID NO: 46 | NRVLNETRSQYEALV |
| SEQ ID NO: 47 | NRVLNETRSQYEAL |
| SEQ ID NO: 48 | LNRVLNETRSQYEAL |
| SEQ ID NO: 49 | NKQVVSSSEQLQSYQAEIIEL |
| SEQ ID NO: 50 | NKQVVSSSEQLQSYQAEIIELR |
| SEQ ID NO: 51 | AEIRSDLE |
| SEQ ID NO: 52 | AEIRSDL |
| SEQ ID NO: 53 | LAEIRSDL |
| SEQ ID NO: 54 | VVQIDNAKLA |
| SEQ ID NO: 55 | VVQIDNAKL |
| SEQ ID NO: 56 | NETRSQYEALV |
| SEQ ID NO: 57 | NKQVVSSSEQLQ |
| SEQ ID NO: 58 | NKQVVSSSEQL |
| SEQ ID NO: 59 | LNKQVVSSSEQL |
| SEQ ID NO: 60 | RQLVESDINGL |
| SEQ ID NO: 61 | SQVQRLITNVESQLA |
| SEQ ID NO: 62 | SQVQRLITNVESQL |
| SEQ ID NO: 63 | NQVLNETRSQYEALV |
| SEQ ID NO: 64 | LNQVLNETRSQYEAL |
| SEQ ID NO: 65 | NQVLNETRSQYEAL |
| SEQ ID NO: 66 | NKQVVSSSEQLQSYQAEIIELR |
| SEQ ID NO: 67 | NKQVVSSSEQLQSYQAEIIEL |
| SEQ ID NO: 68 | VVNIDNAKLA |
| SEQ ID NO: 69 | VVNIDNAKL |
| SEQ ID NO: 70 | NETRSQYEALV |
| SEQ ID NO: 71 | NKQVVSSSEQLQ |
| SEQ ID NO: 72 | NKQVVSSSEQL |
| SEQ ID NO: 73 | LNKQVVSSSEQL |
| SEQ ID NO: 74 | VVNIDNAKLASDDF |
| SEQ ID NO: 75 | SQVQSLITNVESQLA |
| SEQ ID NO: 76 | SQVQSLITNVESQL |
| SEQ ID NO: 77 | NQVLNETRSQYEALV |
| SEQ ID NO: 78 | LNQVLNETRSQYEAL |
| SEQ ID NO: 79 | NQVLNETRSQYEAL |
| SEQ ID NO: 80 | LGRVTIAQGGVL |
| SEQ ID NO: 81 | PKKTESHHKAKGK |
| SEQ ID NO: 82 | IDKVRF |
| SEQ ID NO: 83 | LEQQNKL |
| SEQ ID NO: 84 | RATAENEF |
| SEQ ID NO: 85 | IREYQEVMNSKLGL |
| SEQ ID NO: 86 | QNQLEKLG |
| SEQ ID NO: 87 | LQNQLEKL |
| SEQ ID NO: 88 | QNQLEKL |
| SEQ ID NO: 89 | LGKVTIAQGGVLP |
| SEQ ID NO: 90 | PKKTESHHKAKGK |
| SEQ ID NO: 91 | YRPWGSGSGFG |
| SEQ ID NO: 92 | YRPWGSGSGF |
| SEQ ID NO: 93 | ERIAGEASRL |
| SEQ ID NO: 94 | AKHAVSEGTKAVTKYTSSK |
| SEQ ID NO: 95 | DRANNQVGLAPVA |
| SEQ ID NO: 96 | FDRANNQVGLAPVA |
| SEQ ID NO: 97 | IGGITGPIAKL |
| SEQ ID NO: 98 | MEARGPGELC |
| SEQ ID NO: 99 | MEARGPGELC |
| SEQ ID NO: 100 | IERIPEL |
| SEQ ID NO: 101 | TVIFDTGSSNL |
| SEQ ID NO: 102 | LIPWVQKPIIF |

TABLE-continued

| Item. | Identified short peptide sequences in the preparation obtained from human hair (amino-acid residues given in the standard single-lettercode) |
|---|---|
| SEQ ID NO: 103 | GKEPLGPAL |
| SEQ ID NO: 104 | IVNTNVPRASVPDGF |
| SEQ ID NO: 105 | MALPVTAL |
| SEQ ID NO: 106 | KVGINYQPPTVVPGGDL |
| SEQ ID NO: 107 | IDTSRHYLPVKIIL |
| SEQ ID NO: 108 | LGRIPSAVGYQPTL |
| SEQ ID NO: 109 | VINGNPITIF |
| SEQ ID NO: 110 | MKSCGVSL |

The preparation was added at 0.1% concentration into the culture media of tumour cells. A parallel control culture was maintained under identical conditions, but without added preparation. The cultures were maintained over a standardised number of days, under typical conditions. The culture medium was exchanged daily both in the control and experimental cultures. In the experimental culture, the new medium always contained 0.1% of the preparation. After seven days, the number of cells was evaluated in the control and experimental cultures. It turned out that in the case of human melanoma cells, in the control culture the number of cells grew 20-fold over 7 days. In the experimental culture containing 0.1% of the preparation, however, the number of cells remained at the initial level from the outset of the culture. In the case of a 4 day culture of urinary bladder tumour cells, a 0.1% addition of preparation in the culture inhibited the growth of the cells to 70% of the control population. In the case of human lymphoma in a 4 day culture, a 0.1% addition of preparation caused a decrease of proliferation to 35% of that of control cells.

EXAMPLE 2

The hair of a 28-year old woman was activated and hydrolysed with pepsin according to the method described in Example I. The portion dissolved as a result of pepsin digestion was lyophilised yielding the preparation for further experiments. The preparation was added at 0.1% concentration into the culture media of tumour cells. A parallel control culture was maintained under identical conditions, but without added preparation. The cultures were maintained over a standardised number of days, under typical conditions. The culture medium was exchanged daily both in the control and experimental cultures. In the experimental culture, the new medium always contained 0.1% of the preparation. After seven days, the number of cells was evaluated in the control and experimental cultures. It turned out that in the case of human melanoma cells, in the control culture the number of cells grew 20-fold over 7 days. In the experimental culture containing 0.1% of the preparation, however, the number of cells remained at the initial level from the outset of the culture. In the case of a 4 day culture of urinary bladder tumour cells, a 0.1% addition of preparation in the culture inhibited the growth of the cells to 50% of the control population. In the case of human lymphoma in a 4 day culture, a 0.1% addition of preparation completely inhibited the proliferation of the cells.

EXAMPLE 3

Murine bristles were activated and pepsin hydrolysed according to the method described in Example I. The portion dissolved as a result of pepsin digestion was lyophilised yielding the preparation for further experiments. The preparation was added at 0.1% concentration into the culture media of tumour cells. A parallel control culture was maintained under identical conditions, but without added preparation. The cultures were maintained over a standardised number of days, under typical conditions. The culture medium was exchanged daily both in the control and experimental cultures. In the experimental culture, the new medium always contained 0.1% of the preparation. After four days, the number of cells was evaluated in the control and experimental cultures. It turned out that in the case of murine melanoma cells, the addition of the preparation completely inhibited the proliferation of the cells.

EXAMPLE 4

From the list of peptides in the hydrolysate, we arbitrarily selected the peptide sequences 91 (YRPWGSGSGFG) and 92 (YRPWGSGSGF). These peptides were synthesized using the standard Fmoc procedure on a solid phase beginning with appropriate Wanga resin derivatives, Fmoc-Gly-Wang or Fmoc-Phe-Wang. To deprotect the protective group we used 2% piperidine w dimethylformamide (DMF). To attach the subsequent amino-acid we used a 1.5 excess of the appropriate Fmoc-amino-acid in the presence of a 1.5-fold excess of HATU (O-azobenzotriazol-1yl)-1,1,3,3-tetramethyluronium hexa fluorophosphate)). After synthesizing the peptide with a sequence corresponding to that of peptides 91 or 92, we treated the resin with 99.5% trifluoroacetic acid for 3 minutes. The acid solution was filtered off and rinsed with two small volumes of acid. The combined filtrates were supplemented with a 5-fold volume of an ethyl-ether and hexane mixture (2:1). The precipitate was drained off and washed with the ethyl ether and hexane mixture. The precipitate was dried and purified chromatographically using high-performance preparative chromatography in a gradient of solution A-0.1% HCl and solution B-methanol. The resulting pure peptides in the form of hydrochlorides were used in biological tests.

The synthetic peptides were examined for their effect on the proliferation of melanoma cells of the line MeW 155. The culture was maintained under standard conditions for 3 days with 4000 cells per well of a 96-well culture plate. After three days, the numbers of cells in the control group increased to 120 000. It turned out that after 3 days of culture, peptide 91 at a concentration of 0.004 mM decreased cell numbers to 55% of the control, and a 0.02 mM concentration decreased the cells to 35%, whereas 0.1 mM was toxic to MeW 155 cells. Peptide 92 at 0.004 mM decreased the number of tumour cells to 65% of the control, a 0.02 mMol concentration decreased the number of cells to 49%, and a concentration of 0.1 mM was toxic to melanoma cells.

The invention claimed is:

1. A method of preparing a composition comprising a peptide, said peptide consisting of an amino acid sequence selected from the group consisting of SEQ ID NO: 91, SEQ ID NO: 92 and a mixture thereof, comprising the steps of:
   (a) providing a keratinous material comprising a material selected from the group consisting of hair, wool, fur, and bristles,
   (b) activating said keratinous material with alkali hydroxide to provide an activated keratinous material,
   (c) enzymatically digesting said activated keratinous material to provide a hydrolyzed mixture,
   (d) separating undigested keratinous material from said hydrolyzed mixture to obtain an aqueous hydrolysate comprising the peptides,
   (e) optionally separating water from said aqueous hydrolysate to obtain a peptide mixture comprising the peptides.

2. The method of claim 1, wherein said activating step (b) comprises treatment with aqueous sodium hydroxide.

3. The method of claim 1, wherein said digesting step (d) comprises treatment with pepsin at a pH of 1.6 to 1.9.

4. The method of claim 1, wherein said water separating step (e) comprises lyophilization.

5. A method of inhibiting the growth of tumor cells in vitro, comprising treating tumor cells with a cell growth-inhibiting amount of a pharmaceutical composition comprising a peptide consisting of an amino acid sequence selected from the group consisting of SEQ ID NO: 91, SEQ ID NO: 92, and a mixture of one or more of said individual peptides wherein said tumor cells are selected from the group consisting of melanoma cells, urinary bladder tumor cells, and human lymphoma cells.

6. The method of claim 5, wherein said cell growth-inhibiting amount is 0.1% based on the culture medium of the peptide mixture, or 0.004 to 0.1 mM in the culture medium of the individual peptide.

7. The method of claim 5, wherein said melanoma cells are selected from the group consisting of human and murine melanoma cells.

8. A method of treating a tumor comprising administering to a subject in need thereof a therapeutically effective amount of pharmaceutical composition comprising a peptide consisting of an amino acid sequence selected from the group consisting of SEQ ID NO: 91, SEQ ID NO: 92, and a mixture thereof, and a suitable carrier, said tumor selected from the group consisting of melanoma, urinary bladder tumor, and human lymphoma.

* * * * *

SEQUENCE LISTING

<160> NUMBER OF SEQ ID NOS: 110

<210> SEQ ID NO 1
<211> LENGTH: 7
<212> TYPE: PRT
<213> ORGANISM: Artificial Sequence
<220> FEATURE:
<223> OTHER INFORMATION: Synthetic

<400> SEQUENCE: 1

Ala Glu Ile Arg Ser Asp Leu
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic

<400> SEQUENCE: 2

Val Val Gln Ile Asp Asn Ala Lys Leu
1               5

<210> SEQ ID NO 3
<211> LENGTH: 10
<212> TYPE: PRT
<213> ORGANISM: Artificial Sequence
<220> FEATURE:
<223> OTHER INFORMATION: Synthetic

<400> SEQUENCE: 3

Leu Val Val Gln Ile Asp Asn Ala Lys Leu
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Synthetic

<400> SEQUENCE: 4

Asn Lys Gln Val Val Ser Ser Ser Glu Gln Leu
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Synthetic

<400> SEQUENCE: 5

Leu Asn Lys Gln Val Val Ser Ser Ser Glu Gln Leu
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Synthetic

<400> SEQUENCE: 6

Arg Gln Leu Val Glu Ser Asp Ile Asn Gly Leu
1               5                   10

```
<210> SEQ ID NO 7
<211> LENGTH: 11
<212> TYPE: PRT
<213> ORGANISM: Artificial Sequence
<220> FEATURE:
<223> OTHER INFORMATION: Synthetic

<400> SEQUENCE: 7

Thr Glu Ser Glu Ala Arg Tyr Ser Ser Gln Leu
1               5                   10

<210> SEQ ID NO 8
<211> LENGTH: 14
<212> TYPE: PRT
<213> ORGANISM: Artificial Sequence
<220> FEATURE:
<223> OTHER INFORMATION: Synthetic

<400> SEQUENCE: 8

Val Val Gln Ile Asp Asn Ala Lys Leu Ala Ala Asp Asp Phe
1               5                   10

<210> SEQ ID NO 9
<211> LENGTH: 14
<212> TYPE: PRT
<213> ORGANISM: Artificial Sequence
<220> FEATURE:
<223> OTHER INFORMATION: Synthetic

<400> SEQUENCE: 9

Asn Arg Val Leu Asn Glu Thr Arg Ser Gln Tyr Glu Ala Leu
1               5                   10

<210> SEQ ID NO 10
<211> LENGTH: 22
<212> TYPE: PRT
<213> ORGANISM: Artificial Sequence
<220> FEATURE:
<223> OTHER INFORMATION: Synthetic

<400> SEQUENCE: 10

Asn Lys Gln Val Val Ser Ser Ser Glu Gln Leu Gln Ser Tyr Gln Ala
1               5                   10                  15

Glu Ile Ile Glu Leu Arg
            20

<210> SEQ ID NO 11
<211> LENGTH: 21
<212> TYPE: PRT
<213> ORGANISM: Artificial Sequence
<220> FEATURE:
<223> OTHER INFORMATION: Synthetic

<400> SEQUENCE: 11

Asn Lys Gln Val Val Ser Ser Ser Glu Gln Leu Gln Ser Tyr Gln Ala
1               5                   10                  15

Glu Ile Ile Glu Leu
            20

<210> SEQ ID NO 12
<211> LENGTH: 22
<212> TYPE: PRT
<213> ORGANISM: Artificial Sequence
<220> FEATURE:
<223> OTHER INFORMATION: Synthetic
```

```
<400> SEQUENCE: 12

Leu Asn Lys Gln Val Val Ser Ser Glu Gln Leu Gln Ser Tyr Gln
1               5                   10                  15

Ala Glu Ile Ile Glu Leu
            20

<210> SEQ ID NO 13
<211> LENGTH: 9
<212> TYPE: PRT
<213> ORGANISM: Artificial Sequence
<220> FEATURE:
<223> OTHER INFORMATION: Synthetic

<400> SEQUENCE: 13

Val Val Asn Ile Asp Asn Ala Lys Leu
1               5

<210> SEQ ID NO 14
<211> LENGTH: 11
<212> TYPE: PRT
<213> ORGANISM: Artificial Sequence
<220> FEATURE:
<223> OTHER INFORMATION: Synthetic

<400> SEQUENCE: 14

Asn Lys Gln Val Val Ser Ser Glu Gln Leu
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Synthetic

<400> SEQUENCE: 15

Leu Asn Lys Gln Val Val Ser Ser Glu Gln Leu
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Synthetic

<400> SEQUENCE: 16

Asn Val Glu Val Asp Thr Ala Pro Thr Val Asp Leu
1               5                   10

<210> SEQ ID NO 17
<211> LENGTH: 14
<212> TYPE: PRT
<213> ORGANISM: Artificial Sequence
<220> FEATURE:
<223> OTHER INFORMATION: Synthetic

<400> SEQUENCE: 17

Val Val Asn Ile Asp Asn Ala Lys Leu Ala Ser Asp Asp Phe
1               5                   10

<210> SEQ ID NO 18
<211> LENGTH: 9
<212> TYPE: PRT
<213> ORGANISM: Artificial Sequence
```

```
<220> FEATURE:
<223> OTHER INFORMATION: Synthetic

<400> SEQUENCE: 18

Val Val Glu Ile Asp Asn Ala Lys Leu
1               5

<210> SEQ ID NO 19
<211> LENGTH: 6
<212> TYPE: PRT
<213> ORGANISM: Artificial Sequence
<220> FEATURE:
<223> OTHER INFORMATION: Synthetic

<400> SEQUENCE: 19

Ile Gln Glu Ile Asp Phe
1               5

<210> SEQ ID NO 20
<211> LENGTH: 6
<212> TYPE: PRT
<213> ORGANISM: Artificial Sequence
<220> FEATURE:
<223> OTHER INFORMATION: Synthetic

<400> SEQUENCE: 20

Ile Asp Lys Val Arg Phe
1               5

<210> SEQ ID NO 21
<211> LENGTH: 7
<212> TYPE: PRT
<213> ORGANISM: Artificial Sequence
<220> FEATURE:
<223> OTHER INFORMATION: Synthetic

<400> SEQUENCE: 21

Leu Glu Gln Gln Asn Lys Leu
1               5

<210> SEQ ID NO 22
<211> LENGTH: 11
<212> TYPE: PRT
<213> ORGANISM: Artificial Sequence
<220> FEATURE:
<223> OTHER INFORMATION: Synthetic

<400> SEQUENCE: 22

Ala Ser Glu Leu Asn His Val Gln Glu Val Leu
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Synthetic

<400> SEQUENCE: 23

Asn Gln Gln Val Val Ser Ser Glu Gln Leu
1               5                   10

<210> SEQ ID NO 24
<211> LENGTH: 11
<212> TYPE: PRT
<213> ORGANISM: Artificial Sequence
<220> FEATURE:
```

<223> OTHER INFORMATION: Synthetic

<400> SEQUENCE: 24

Asn Gln Gln Val Val Ser Ser Ser Glu Gln Leu
1               5                   10

<210> SEQ ID NO 25
<211> LENGTH: 11
<212> TYPE: PRT
<213> ORGANISM: Artificial Sequence
<220> FEATURE:
<223> OTHER INFORMATION: Synthetic

<400> SEQUENCE: 25

Arg Gln Leu Val Glu Ser Asp Ile Asn Gly Leu
1               5                   10

<210> SEQ ID NO 26
<211> LENGTH: 14
<212> TYPE: PRT
<213> ORGANISM: Artificial Sequence
<220> FEATURE:
<223> OTHER INFORMATION: Synthetic

<400> SEQUENCE: 26

Val Val Glu Ile Asp Asn Ala Lys Leu Ala Ala Asp Asp Phe
1               5                   10

<210> SEQ ID NO 27
<211> LENGTH: 14
<212> TYPE: PRT
<213> ORGANISM: Artificial Sequence
<220> FEATURE:
<223> OTHER INFORMATION: Synthetic

<400> SEQUENCE: 27

Ile Val Gln Ile Asp Asn Ala Lys Leu Ala Ala Asp Asp Phe
1               5                   10

<210> SEQ ID NO 28
<211> LENGTH: 11
<212> TYPE: PRT
<213> ORGANISM: Artificial Sequence
<220> FEATURE:
<223> OTHER INFORMATION: Synthetic

<400> SEQUENCE: 28

Thr Val Ile Phe Asp Thr Gly Ser Ser Asn Leu
1               5                   10

<210> SEQ ID NO 29
<211> LENGTH: 15
<212> TYPE: PRT
<213> ORGANISM: Artificial Sequence
<220> FEATURE:
<223> OTHER INFORMATION: Synthetic

<400> SEQUENCE: 29

Gly Ile Leu Gly Pro Val Ile Lys Ala Glu Val Gly Asp Thr Leu
1               5                   10                  15

<210> SEQ ID NO 30
<211> LENGTH: 6
<212> TYPE: PRT
<213> ORGANISM: Artificial Sequence
<220> FEATURE:
<223> OTHER INFORMATION: Synthetic

<400> SEQUENCE: 30

Ile Gln Glu Ile Asp Phe
1               5

<210> SEQ ID NO 31
<211> LENGTH: 6
<212> TYPE: PRT
<213> ORGANISM: Artificial Sequence
<220> FEATURE:
<223> OTHER INFORMATION: Synthetic

<400> SEQUENCE: 31

Ile Asp Lys Val Arg Phe
1               5

<210> SEQ ID NO 32
<211> LENGTH: 9
<212> TYPE: PRT
<213> ORGANISM: Artificial Sequence
<220> FEATURE:
<223> OTHER INFORMATION: Synthetic

<400> SEQUENCE: 32

Val Val Gln Ile Asp Asn Ala Lys Leu
1               5

<210> SEQ ID NO 33
<211> LENGTH: 7
<212> TYPE: PRT
<213> ORGANISM: Artificial Sequence
<220> FEATURE:
<223> OTHER INFORMATION: Synthetic

<400> SEQUENCE: 33

Ala Glu Ile Arg Ser Asp Leu
1               5

<210> SEQ ID NO 34
<211> LENGTH: 8
<212> TYPE: PRT
<213> ORGANISM: Artificial Sequence
<220> FEATURE:
<223> OTHER INFORMATION: Synthetic

<400> SEQUENCE: 34

Ala Glu Ile Arg Ser Asp Leu Glu
1               5

<210> SEQ ID NO 35
<211> LENGTH: 7
<212> TYPE: PRT
<213> ORGANISM: Artificial Sequence
<220> FEATURE:
<223> OTHER INFORMATION: Synthetic

<400> SEQUENCE: 35

Ala Glu Ile Arg Ser Asp Leu
1               5

<210> SEQ ID NO 36
<211> LENGTH: 10
<212> TYPE: PRT
<213> ORGANISM: Artificial Sequence
<220> FEATURE:
<223> OTHER INFORMATION: Synthetic

```
<400> SEQUENCE: 36

Val Val Gln Ile Asp Asn Ala Lys Leu Ala
1               5                   10

<210> SEQ ID NO 37
<211> LENGTH: 9
<212> TYPE: PRT
<213> ORGANISM: Artificial Sequence
<220> FEATURE:
<223> OTHER INFORMATION: Synthetic

<400> SEQUENCE: 37

Val Val Gln Ile Asp Asn Ala Lys Leu
1               5

<210> SEQ ID NO 38
<211> LENGTH: 10
<212> TYPE: PRT
<213> ORGANISM: Artificial Sequence
<220> FEATURE:
<223> OTHER INFORMATION: Synthetic

<400> SEQUENCE: 38

Asn Glu Thr Arg Ser Gln Tyr Glu Ala Leu
1               5                   10

<210> SEQ ID NO 39
<211> LENGTH: 12
<212> TYPE: PRT
<213> ORGANISM: Artificial Sequence
<220> FEATURE:
<223> OTHER INFORMATION: Synthetic

<400> SEQUENCE: 39

Asn Lys Gln Val Val Ser Ser Ser Glu Gln Leu Gln
1               5                   10

<210> SEQ ID NO 40
<211> LENGTH: 11
<212> TYPE: PRT
<213> ORGANISM: Artificial Sequence
<220> FEATURE:
<223> OTHER INFORMATION: Synthetic

<400> SEQUENCE: 40

Asn Lys Gln Val Val Ser Ser Ser Glu Gln Leu
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Synthetic

<400> SEQUENCE: 41

Leu Asn Lys Gln Val Val Ser Ser Ser Glu Gln Leu
1               5                   10

<210> SEQ ID NO 42
<211> LENGTH: 11
<212> TYPE: PRT
<213> ORGANISM: Artificial Sequence
<220> FEATURE:
<223> OTHER INFORMATION: Synthetic

<400> SEQUENCE: 42
```

```
Arg Gln Leu Val Glu Ser Asp Ile Asn Gly Leu
1               5                   10

<210> SEQ ID NO 43
<211> LENGTH: 14
<212> TYPE: PRT
<213> ORGANISM: Artificial Sequence
<220> FEATURE:
<223> OTHER INFORMATION: Synthetic

<400> SEQUENCE: 43

Val Val Gln Ile Asp Asn Ala Lys Leu Ala Ala Asp Asp Phe
1               5                   10

<210> SEQ ID NO 44
<211> LENGTH: 14
<212> TYPE: PRT
<213> ORGANISM: Artificial Sequence
<220> FEATURE:
<223> OTHER INFORMATION: Synthetic

<400> SEQUENCE: 44

Ser Gln Val Gln Ser Leu Ile Thr Asn Val Glu Ser Gln Leu
1               5                   10

<210> SEQ ID NO 45
<211> LENGTH: 15
<212> TYPE: PRT
<213> ORGANISM: Artificial Sequence
<220> FEATURE:
<223> OTHER INFORMATION: Synthetic

<400> SEQUENCE: 45

Ser Gln Val Gln Ser Leu Ile Thr Asn Val Glu Ser Gln Leu Ala
1               5                   10                  15

<210> SEQ ID NO 46
<211> LENGTH: 15
<212> TYPE: PRT
<213> ORGANISM: Artificial Sequence
<220> FEATURE:
<223> OTHER INFORMATION: Synthetic

<400> SEQUENCE: 46

Asn Arg Val Leu Asn Glu Thr Arg Ser Gln Tyr Glu Ala Leu Val
1               5                   10                  15

<210> SEQ ID NO 47
<211> LENGTH: 14
<212> TYPE: PRT
<213> ORGANISM: Artificial Sequence
<220> FEATURE:
<223> OTHER INFORMATION: Synthetic

<400> SEQUENCE: 47

Asn Arg Val Leu Asn Glu Thr Arg Ser Gln Tyr Glu Ala Leu
1               5                   10

<210> SEQ ID NO 48
<211> LENGTH: 15
<212> TYPE: PRT
<213> ORGANISM: Artificial Sequence
<220> FEATURE:
<223> OTHER INFORMATION: Synthetic

<400> SEQUENCE: 48
```

```
Leu Asn Arg Val Leu Asn Glu Thr Arg Ser Gln Tyr Glu Ala Leu
1               5                   10                  15

<210> SEQ ID NO 49
<211> LENGTH: 21
<212> TYPE: PRT
<213> ORGANISM: Artificial Sequence
<220> FEATURE:
<223> OTHER INFORMATION: Synthetic

<400> SEQUENCE: 49

Asn Lys Gln Val Val Ser Ser Ser Glu Gln Leu Gln Ser Tyr Gln Ala
1               5                   10                  15

Glu Ile Ile Glu Leu
            20

<210> SEQ ID NO 50
<211> LENGTH: 22
<212> TYPE: PRT
<213> ORGANISM: Artificial Sequence
<220> FEATURE:
<223> OTHER INFORMATION: Synthetic

<400> SEQUENCE: 50

Asn Lys Gln Val Val Ser Ser Ser Glu Gln Leu Gln Ser Tyr Gln Ala
1               5                   10                  15

Glu Ile Ile Glu Leu Arg
            20

<210> SEQ ID NO 51
<211> LENGTH: 8
<212> TYPE: PRT
<213> ORGANISM: Artificial Sequence
<220> FEATURE:
<223> OTHER INFORMATION: Synthetic

<400> SEQUENCE: 51

Ala Glu Ile Arg Ser Asp Leu Glu
1               5

<210> SEQ ID NO 52
<211> LENGTH: 7
<212> TYPE: PRT
<213> ORGANISM: Artificial Sequence
<220> FEATURE:
<223> OTHER INFORMATION: Synthetic

<400> SEQUENCE: 52

Ala Glu Ile Arg Ser Asp Leu
1               5

<210> SEQ ID NO 53
<211> LENGTH: 8
<212> TYPE: PRT
<213> ORGANISM: Artificial Sequence
<220> FEATURE:
<223> OTHER INFORMATION: Synthetic

<400> SEQUENCE: 53

Leu Ala Glu Ile Arg Ser Asp Leu
1               5

<210> SEQ ID NO 54
<211> LENGTH: 10
<212> TYPE: PRT
<213> ORGANISM: Artificial Sequence
```

```
<220> FEATURE:
<223> OTHER INFORMATION: Synthetic

<400> SEQUENCE: 54

Val Val Gln Ile Asp Asn Ala Lys Leu Ala
1               5                   10

<210> SEQ ID NO 55
<211> LENGTH: 9
<212> TYPE: PRT
<213> ORGANISM: Artificial Sequence
<220> FEATURE:
<223> OTHER INFORMATION: Synthetic

<400> SEQUENCE: 55

Val Val Gln Ile Asp Asn Ala Lys Leu
1               5

<210> SEQ ID NO 56
<211> LENGTH: 11
<212> TYPE: PRT
<213> ORGANISM: Artificial Sequence
<220> FEATURE:
<223> OTHER INFORMATION: Synthetic

<400> SEQUENCE: 56

Asn Glu Thr Arg Ser Gln Tyr Glu Ala Leu Val
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Synthetic

<400> SEQUENCE: 57

Asn Lys Gln Val Val Ser Ser Ser Glu Gln Leu Gln
1               5                   10

<210> SEQ ID NO 58
<211> LENGTH: 11
<212> TYPE: PRT
<213> ORGANISM: Artificial Sequence
<220> FEATURE:
<223> OTHER INFORMATION: Synthetic

<400> SEQUENCE: 58

Asn Lys Gln Val Val Ser Ser Ser Glu Gln Leu
1               5                   10

<210> SEQ ID NO 59
<211> LENGTH: 12
<212> TYPE: PRT
<213> ORGANISM: Artificial Sequence
<220> FEATURE:
<223> OTHER INFORMATION: Synthetic

<400> SEQUENCE: 59

Leu Asn Lys Gln Val Val Ser Ser Ser Glu Gln Leu
1               5                   10

<210> SEQ ID NO 60
<211> LENGTH: 11
<212> TYPE: PRT
<213> ORGANISM: Artificial Sequence
<220> FEATURE:
```

```
<223> OTHER INFORMATION: Synthetic

<400> SEQUENCE: 60

Arg Gln Leu Val Glu Ser Asp Ile Asn Gly Leu
1               5                   10

<210> SEQ ID NO 61
<211> LENGTH: 15
<212> TYPE: PRT
<213> ORGANISM: Artificial Sequence
<220> FEATURE:
<223> OTHER INFORMATION: Synthetic

<400> SEQUENCE: 61

Ser Gln Val Gln Arg Leu Ile Thr Asn Val Glu Ser Gln Leu Ala
1               5                   10                  15

<210> SEQ ID NO 62
<211> LENGTH: 14
<212> TYPE: PRT
<213> ORGANISM: Artificial Sequence
<220> FEATURE:
<223> OTHER INFORMATION: Synthetic

<400> SEQUENCE: 62

Ser Gln Val Gln Arg Leu Ile Thr Asn Val Glu Ser Gln Leu
1               5                   10

<210> SEQ ID NO 63
<211> LENGTH: 15
<212> TYPE: PRT
<213> ORGANISM: Artificial Sequence
<220> FEATURE:
<223> OTHER INFORMATION: Synthetic

<400> SEQUENCE: 63

Asn Gln Val Leu Asn Glu Thr Arg Ser Gln Tyr Glu Ala Leu Val
1               5                   10                  15

<210> SEQ ID NO 64
<211> LENGTH: 15
<212> TYPE: PRT
<213> ORGANISM: Artificial Sequence
<220> FEATURE:
<223> OTHER INFORMATION: Synthetic

<400> SEQUENCE: 64

Leu Asn Gln Val Leu Asn Glu Thr Arg Ser Gln Tyr Glu Ala Leu
1               5                   10                  15

<210> SEQ ID NO 65
<211> LENGTH: 14
<212> TYPE: PRT
<213> ORGANISM: Artificial Sequence
<220> FEATURE:
<223> OTHER INFORMATION: Synthetic

<400> SEQUENCE: 65

Asn Gln Val Leu Asn Glu Thr Arg Ser Gln Tyr Glu Ala Leu
1               5                   10

<210> SEQ ID NO 66
<211> LENGTH: 22
<212> TYPE: PRT
<213> ORGANISM: Artificial Sequence
<220> FEATURE:
<223> OTHER INFORMATION: Synthetic
```

<400> SEQUENCE: 66

Asn Lys Gln Val Val Ser Ser Ser Glu Gln Leu Gln Ser Tyr Gln Ala
1               5                   10                  15
Glu Ile Ile Glu Leu Arg
            20

<210> SEQ ID NO 67
<211> LENGTH: 21
<212> TYPE: PRT
<213> ORGANISM: Artificial Sequence
<220> FEATURE:
<223> OTHER INFORMATION: Synthetic

<400> SEQUENCE: 67

Asn Lys Gln Val Val Ser Ser Ser Glu Gln Leu Gln Ser Tyr Gln Ala
1               5                   10                  15
Glu Ile Ile Glu Leu
            20

<210> SEQ ID NO 68
<211> LENGTH: 10
<212> TYPE: PRT
<213> ORGANISM: Artificial Sequence
<220> FEATURE:
<223> OTHER INFORMATION: Synthetic

<400> SEQUENCE: 68

Val Val Asn Ile Asp Asn Ala Lys Leu Ala
1               5                   10

<210> SEQ ID NO 69
<211> LENGTH: 9
<212> TYPE: PRT
<213> ORGANISM: Artificial Sequence
<220> FEATURE:
<223> OTHER INFORMATION: Synthetic

<400> SEQUENCE: 69

Val Val Asn Ile Asp Asn Ala Lys Leu
1               5

<210> SEQ ID NO 70
<211> LENGTH: 11
<212> TYPE: PRT
<213> ORGANISM: Artificial Sequence
<220> FEATURE:
<223> OTHER INFORMATION: Synthetic

<400> SEQUENCE: 70

Asn Glu Thr Arg Ser Gln Tyr Glu Ala Leu Val
1               5                   10

<210> SEQ ID NO 71
<211> LENGTH: 12
<212> TYPE: PRT
<213> ORGANISM: Artificial Sequence
<220> FEATURE:
<223> OTHER INFORMATION: Synthetic

<400> SEQUENCE: 71

Asn Lys Gln Val Val Ser Ser Ser Glu Gln Leu Gln
1               5                   10

<210> SEQ ID NO 72

```
<211> LENGTH: 11
<212> TYPE: PRT
<213> ORGANISM: Artificial Sequence
<220> FEATURE:
<223> OTHER INFORMATION: Synthetic

<400> SEQUENCE: 72

Asn Lys Gln Val Val Ser Ser Ser Glu Gln Leu
1               5                   10

<210> SEQ ID NO 73
<211> LENGTH: 12
<212> TYPE: PRT
<213> ORGANISM: Artificial Sequence
<220> FEATURE:
<223> OTHER INFORMATION: Synthetic

<400> SEQUENCE: 73

Leu Asn Lys Gln Val Val Ser Ser Ser Glu Gln Leu
1               5                   10

<210> SEQ ID NO 74
<211> LENGTH: 14
<212> TYPE: PRT
<213> ORGANISM: Artificial Sequence
<220> FEATURE:
<223> OTHER INFORMATION: Synthetic

<400> SEQUENCE: 74

Val Val Asn Ile Asp Asn Ala Lys Leu Ala Ser Asp Asp Phe
1               5                   10

<210> SEQ ID NO 75
<211> LENGTH: 15
<212> TYPE: PRT
<213> ORGANISM: Artificial Sequence
<220> FEATURE:
<223> OTHER INFORMATION: Synthetic

<400> SEQUENCE: 75

Ser Gln Val Gln Ser Leu Ile Thr Asn Val Glu Ser Gln Leu Ala
1               5                   10                  15

<210> SEQ ID NO 76
<211> LENGTH: 14
<212> TYPE: PRT
<213> ORGANISM: Artificial Sequence
<220> FEATURE:
<223> OTHER INFORMATION: Synthetic

<400> SEQUENCE: 76

Ser Gln Val Gln Ser Leu Ile Thr Asn Val Glu Ser Gln Leu
1               5                   10

<210> SEQ ID NO 77
<211> LENGTH: 15
<212> TYPE: PRT
<213> ORGANISM: Artificial Sequence
<220> FEATURE:
<223> OTHER INFORMATION: Synthetic

<400> SEQUENCE: 77

Asn Gln Val Leu Asn Glu Thr Arg Ser Gln Tyr Glu Ala Leu Val
1               5                   10                  15

<210> SEQ ID NO 78
<211> LENGTH: 15
```

```
<212> TYPE: PRT
<213> ORGANISM: Artificial Sequence
<220> FEATURE:
<223> OTHER INFORMATION: Synthetic

<400> SEQUENCE: 78

Leu Asn Gln Val Leu Asn Glu Thr Arg Ser Gln Tyr Glu Ala Leu
 1               5                  10                  15

<210> SEQ ID NO 79
<211> LENGTH: 14
<212> TYPE: PRT
<213> ORGANISM: Artificial Sequence
<220> FEATURE:
<223> OTHER INFORMATION: Synthetic

<400> SEQUENCE: 79

Asn Gln Val Leu Asn Glu Thr Arg Ser Gln Tyr Glu Ala Leu
 1               5                  10

<210> SEQ ID NO 80
<211> LENGTH: 12
<212> TYPE: PRT
<213> ORGANISM: Artificial Sequence
<220> FEATURE:
<223> OTHER INFORMATION: Synthetic

<400> SEQUENCE: 80

Leu Gly Arg Val Thr Ile Ala Gln Gly Gly Val Leu
 1               5                  10

<210> SEQ ID NO 81
<211> LENGTH: 13
<212> TYPE: PRT
<213> ORGANISM: Artificial Sequence
<220> FEATURE:
<223> OTHER INFORMATION: Synthetic

<400> SEQUENCE: 81

Pro Lys Lys Thr Glu Ser His His Lys Ala Lys Gly Lys
 1               5                  10

<210> SEQ ID NO 82
<211> LENGTH: 6
<212> TYPE: PRT
<213> ORGANISM: Artificial Sequence
<220> FEATURE:
<223> OTHER INFORMATION: Synthetic

<400> SEQUENCE: 82

Ile Asp Lys Val Arg Phe
 1               5

<210> SEQ ID NO 83
<211> LENGTH: 7
<212> TYPE: PRT
<213> ORGANISM: Artificial Sequence
<220> FEATURE:
<223> OTHER INFORMATION: Synthetic

<400> SEQUENCE: 83

Leu Glu Gln Gln Asn Lys Leu
 1               5

<210> SEQ ID NO 84
<211> LENGTH: 8
<212> TYPE: PRT
```

```
<213> ORGANISM: Artificial Sequence
<220> FEATURE:
<223> OTHER INFORMATION: Synthetic

<400> SEQUENCE: 84

Arg Ala Thr Ala Glu Asn Glu Phe
1               5

<210> SEQ ID NO 85
<211> LENGTH: 14
<212> TYPE: PRT
<213> ORGANISM: Artificial Sequence
<220> FEATURE:
<223> OTHER INFORMATION: Synthetic

<400> SEQUENCE: 85

Ile Arg Glu Tyr Gln Glu Val Met Asn Ser Lys Leu Gly Leu
1               5                   10

<210> SEQ ID NO 86
<211> LENGTH: 8
<212> TYPE: PRT
<213> ORGANISM: Artificial Sequence
<220> FEATURE:
<223> OTHER INFORMATION: Synthetic

<400> SEQUENCE: 86

Gln Asn Gln Leu Glu Lys Leu Gly
1               5

<210> SEQ ID NO 87
<211> LENGTH: 8
<212> TYPE: PRT
<213> ORGANISM: Artificial Sequence
<220> FEATURE:
<223> OTHER INFORMATION: Synthetic

<400> SEQUENCE: 87

Leu Gln Asn Gln Leu Glu Lys Leu
1               5

<210> SEQ ID NO 88
<211> LENGTH: 7
<212> TYPE: PRT
<213> ORGANISM: Artificial Sequence
<220> FEATURE:
<223> OTHER INFORMATION: Synthetic

<400> SEQUENCE: 88

Gln Asn Gln Leu Glu Lys Leu
1               5

<210> SEQ ID NO 89
<211> LENGTH: 13
<212> TYPE: PRT
<213> ORGANISM: Artificial Sequence
<220> FEATURE:
<223> OTHER INFORMATION: Synthetic

<400> SEQUENCE: 89

Leu Gly Lys Val Thr Ile Ala Gln Gly Gly Val Leu Pro
1               5                   10

<210> SEQ ID NO 90
<211> LENGTH: 13
<212> TYPE: PRT
<213> ORGANISM: Artificial Sequence
```

```
<220> FEATURE:
<223> OTHER INFORMATION: Synthetic

<400> SEQUENCE: 90

Pro Lys Lys Thr Glu Ser His His Lys Ala Lys Gly Lys
1               5                   10

<210> SEQ ID NO 91
<211> LENGTH: 11
<212> TYPE: PRT
<213> ORGANISM: Artificial Sequence
<220> FEATURE:
<223> OTHER INFORMATION: Synthetic

<400> SEQUENCE: 91

Tyr Arg Pro Trp Gly Ser Gly Ser Gly Phe Gly
1               5                   10

<210> SEQ ID NO 92
<211> LENGTH: 10
<212> TYPE: PRT
<213> ORGANISM: Artificial Sequence
<220> FEATURE:
<223> OTHER INFORMATION: Synthetic

<400> SEQUENCE: 92

Tyr Arg Pro Trp Gly Ser Gly Ser Gly Phe
1               5                   10

<210> SEQ ID NO 93
<211> LENGTH: 10
<212> TYPE: PRT
<213> ORGANISM: Artificial Sequence
<220> FEATURE:
<223> OTHER INFORMATION: Synthetic

<400> SEQUENCE: 93

Glu Arg Ile Ala Gly Glu Ala Ser Arg Leu
1               5                   10

<210> SEQ ID NO 94
<211> LENGTH: 19
<212> TYPE: PRT
<213> ORGANISM: Artificial Sequence
<220> FEATURE:
<223> OTHER INFORMATION: Synthetic

<400> SEQUENCE: 94

Ala Lys His Ala Val Ser Glu Gly Thr Lys Ala Val Thr Lys Tyr Thr
1               5                   10                  15

Ser Ser Lys

<210> SEQ ID NO 95
<211> LENGTH: 13
<212> TYPE: PRT
<213> ORGANISM: Artificial Sequence
<220> FEATURE:
<223> OTHER INFORMATION: Synthetic

<400> SEQUENCE: 95

Asp Arg Ala Asn Asn Gln Val Gly Leu Ala Pro Val Ala
1               5                   10

<210> SEQ ID NO 96
<211> LENGTH: 14
<212> TYPE: PRT
```

```
<213> ORGANISM: Artificial Sequence
<220> FEATURE:
<223> OTHER INFORMATION: Synthetic

<400> SEQUENCE: 96

Phe Asp Arg Ala Asn Asn Gln Val Gly Leu Ala Pro Val Ala
1               5                   10

<210> SEQ ID NO 97
<211> LENGTH: 11
<212> TYPE: PRT
<213> ORGANISM: Artificial Sequence
<220> FEATURE:
<223> OTHER INFORMATION: Synthetic

<400> SEQUENCE: 97

Ile Gly Gly Ile Thr Gly Pro Ile Ala Lys Leu
1               5                   10

<210> SEQ ID NO 98
<211> LENGTH: 10
<212> TYPE: PRT
<213> ORGANISM: Artificial Sequence
<220> FEATURE:
<223> OTHER INFORMATION: Synthetic

<400> SEQUENCE: 98

Met Glu Ala Arg Gly Pro Gly Glu Leu Cys
1               5                   10

<210> SEQ ID NO 99
<211> LENGTH: 10
<212> TYPE: PRT
<213> ORGANISM: Artificial Sequence
<220> FEATURE:
<223> OTHER INFORMATION: Synthetic

<400> SEQUENCE: 99

Met Glu Ala Arg Gly Pro Gly Glu Leu Cys
1               5                   10

<210> SEQ ID NO 100
<211> LENGTH: 7
<212> TYPE: PRT
<213> ORGANISM: Artificial Sequence
<220> FEATURE:
<223> OTHER INFORMATION: Synthetic

<400> SEQUENCE: 100

Ile Glu Arg Ile Pro Glu Leu
1               5

<210> SEQ ID NO 101
<211> LENGTH: 11
<212> TYPE: PRT
<213> ORGANISM: Artificial Sequence
<220> FEATURE:
<223> OTHER INFORMATION: Synthetic

<400> SEQUENCE: 101

Thr Val Ile Phe Asp Thr Gly Ser Ser Asn Leu
1               5                   10

<210> SEQ ID NO 102
<211> LENGTH: 11
<212> TYPE: PRT
<213> ORGANISM: Artificial Sequence
```

<220> FEATURE:
<223> OTHER INFORMATION: Synthetic

<400> SEQUENCE: 102

Leu Ile Pro Trp Val Gln Lys Pro Ile Ile Phe
1               5                   10

<210> SEQ ID NO 103
<211> LENGTH: 9
<212> TYPE: PRT
<213> ORGANISM: Artificial Sequence
<220> FEATURE:
<223> OTHER INFORMATION: Synthetic

<400> SEQUENCE: 103

Gly Lys Glu Pro Leu Gly Pro Ala Leu
1               5

<210> SEQ ID NO 104
<211> LENGTH: 15
<212> TYPE: PRT
<213> ORGANISM: Artificial Sequence
<220> FEATURE:
<223> OTHER INFORMATION: Synthetic

<400> SEQUENCE: 104

Ile Val Asn Thr Asn Val Pro Arg Ala Ser Val Pro Asp Gly Phe
1               5                   10                  15

<210> SEQ ID NO 105
<211> LENGTH: 8
<212> TYPE: PRT
<213> ORGANISM: Artificial Sequence
<220> FEATURE:
<223> OTHER INFORMATION: Synthetic

<400> SEQUENCE: 105

Met Ala Leu Pro Val Thr Ala Leu
1               5

<210> SEQ ID NO 106
<211> LENGTH: 17
<212> TYPE: PRT
<213> ORGANISM: Artificial Sequence
<220> FEATURE:
<223> OTHER INFORMATION: Synthetic

<400> SEQUENCE: 106

Lys Val Gly Ile Asn Tyr Gln Pro Pro Thr Val Val Pro Gly Gly Asp
1               5                   10                  15
Leu

<210> SEQ ID NO 107
<211> LENGTH: 14
<212> TYPE: PRT
<213> ORGANISM: Artificial Sequence
<220> FEATURE:
<223> OTHER INFORMATION: Synthetic

<400> SEQUENCE: 107

Ile Asp Thr Ser Arg His Tyr Leu Pro Val Lys Ile Ile Leu
1               5                   10

<210> SEQ ID NO 108
<211> LENGTH: 14
<212> TYPE: PRT

```
<213> ORGANISM: Artificial Sequence
<220> FEATURE:
<223> OTHER INFORMATION: Synthetic

<400> SEQUENCE: 108

Leu Gly Arg Ile Pro Ser Ala Val Gly Tyr Gln Pro Thr Leu
1               5                   10

<210> SEQ ID NO 109
<211> LENGTH: 10
<212> TYPE: PRT
<213> ORGANISM: Artificial Sequence
<220> FEATURE:
<223> OTHER INFORMATION: Synthetic

<400> SEQUENCE: 109

Val Ile Asn Gly Asn Pro Ile Thr Ile Phe
1               5                   10

<210> SEQ ID NO 110
<211> LENGTH: 8
<212> TYPE: PRT
<213> ORGANISM: Artificial Sequence
<220> FEATURE:
<223> OTHER INFORMATION: Synthetic

<400> SEQUENCE: 110

Met Lys Ser Cys Gly Val Ser Leu
1               5
```